（12） United States Patent
Dorn et al.

(10) Patent No.: US 10,993,822 B2
(45) Date of Patent: May 4, 2021

(54) HAND-HELD ACTUATOR DEVICE (71) Applicant: C. R. Bard, Inc., Tempe, AZ (US)

(72) Inventors: Jurgen Dorn, Neulussheim (DE);
Martin Wubbeling, Mannheim (DE);
Michael Vogel, Karlsruhe (DE)

(73) Assignee: C. R. Bard, Inc., Franklin Lakes, NJ (US)

( * ) Notice: Subject to any disclaimer, the term of this patent is extended or adjusted under 35 U.S.C. 154(b) by 114 days.

(21) Appl. No.: 15/901,185

(22) Filed: Feb. 21, 2018

(65) Prior Publication Data

US 2018/0177621 A1    Jun. 28, 2018

Related U.S. Application Data

(60) Continuation of application No. 14/793,669, filed on Jul. 7, 2015, now Pat. No. 9,901,469, which is a division of application No. 12/376,670, filed as application No. PCT/EP2007/058205 on Aug. 7, 2007, now Pat. No. 9,078,779.

(30) Foreign Application Priority Data

Aug. 7, 2006 (GB) .................................. 0615658

(51) Int. Cl.
*A61F 2/95* (2013.01)
*A61F 2/966* (2013.01)
*A61F 2/962* (2013.01)
*A61M 25/01* (2006.01)
*A61F 2/92* (2013.01)

(52) U.S. Cl.
CPC ................ *A61F 2/95* (2013.01); *A61F 2/962* (2013.01); *A61F 2/966* (2013.01); *A61F 2/92* (2013.01); *A61F 2/9517* (2020.05); *A61M 25/0147* (2013.01); *A61M 2025/015* (2013.01)

(58) Field of Classification Search
CPC .. A61F 2/95; A61F 2/962; A61F 2/966; A61F 2/9517
See application file for complete search history.

(56) References Cited

U.S. PATENT DOCUMENTS

| 1,988,060 A | 1/1935 | Vollenbroich |
| 2,831,356 A | 4/1958 | Wiman |

(Continued)

FOREIGN PATENT DOCUMENTS

| CA | 2155527 A1 | 8/1994 |
| DE | 1775056 A1 | 3/1972 |

(Continued)

OTHER PUBLICATIONS

"Summary for the Bridge SE Biliary Self-Expanding Stent Delivery System" Jan. 14, 2002 FDA Section 51 O (k) review.

(Continued)

*Primary Examiner* — Richard G Louis
(74) *Attorney, Agent, or Firm* — Rutan & Tucker LLP (57) ABSTRACT

A hand-held actuator device for releasing into the body from a delivery system a medical prosthesis, like a stent, comprising a frame that acts as a housing, a reel for receiving a wire, a manually operable slider mounted to the frame and a one-way connection between the slider and the reel. Actuating the slider causes the reel to wind up the wire and release the medical prosthesis.

8 Claims, 3 Drawing Sheets

(56) References Cited

U.S. PATENT DOCUMENTS

| | | |
|---|---|---|
| 2,934,211 A | 4/1960 | Shivek |
| 2,939,680 A | 6/1960 | Powell |
| 3,070,057 A | 12/1962 | Dezzani |
| 3,137,176 A | 6/1964 | Wright |
| 3,562,427 A | 2/1971 | Yano |
| 3,585,707 A | 6/1971 | Stevens |
| 3,871,382 A | 3/1975 | Mann |
| 3,881,423 A | 5/1975 | Woods et al. |
| 4,256,113 A | 3/1981 | Chamness |
| 4,553,545 A | 11/1985 | Maass et al. |
| 4,580,568 A | 4/1986 | Gianturco |
| 4,616,648 A | 10/1986 | Simpson |
| 4,649,922 A | 3/1987 | Wiktor |
| 4,665,918 A | 5/1987 | Garza et al. |
| 4,723,547 A | 2/1988 | Kullas |
| 4,733,665 A | 3/1988 | Palmaz |
| 4,739,762 A | 4/1988 | Palmaz |
| 4,748,982 A | 6/1988 | Horzewski et al. |
| 4,760,622 A | 8/1988 | Rohrman |
| 4,771,773 A | 9/1988 | Kropf |
| 4,800,882 A | 1/1989 | Gianturco |
| 4,856,516 A | 8/1989 | Hillstead |
| 4,886,062 A | 12/1989 | Wiktor |
| 4,889,112 A | 12/1989 | Schachner et al. |
| 4,913,141 A | 4/1990 | Hillstead |
| 4,913,683 A | 4/1990 | Gregory |
| 4,921,483 A | 5/1990 | Wijay et al. |
| 4,969,458 A | 11/1990 | Wiktor |
| 4,990,151 A | 2/1991 | Wallsten |
| 5,019,090 A | 5/1991 | Pinchuk |
| 5,026,377 A | 6/1991 | Burton et al. |
| 5,045,072 A | 9/1991 | Castillo et al. |
| 5,049,128 A | 9/1991 | Duquette |
| 5,054,162 A | 10/1991 | Rogers |
| 5,102,417 A | 4/1992 | Palmaz |
| 5,104,404 A | 4/1992 | Wolff |
| 5,116,365 A | 5/1992 | Hillstead |
| 5,133,732 A | 7/1992 | Wiktor |
| 5,135,536 A | 8/1992 | Hillstead |
| 5,161,547 A | 11/1992 | Tower |
| 5,163,941 A | 11/1992 | Garth |
| 5,190,552 A | 3/1993 | Kelman |
| 5,201,757 A | 4/1993 | Heyn et al. |
| 5,203,774 A | 4/1993 | Gilson et al. |
| 5,209,754 A | 5/1993 | Ahluwalia |
| 5,224,939 A | 7/1993 | Holman et al. |
| 5,228,452 A | 7/1993 | Samson |
| 5,242,423 A | 9/1993 | Goodsir et al. |
| 5,254,107 A | 10/1993 | Soltesz et al. |
| 5,275,622 A | 1/1994 | Lazarus et al. |
| 5,279,596 A | 1/1994 | Castaneda et al. |
| 5,282,824 A | 2/1994 | Gianturco |
| 5,290,295 A | 3/1994 | Querals et al. |
| 5,290,310 A | 3/1994 | Makower et al. |
| 5,292,331 A | 3/1994 | Boneau |
| 5,312,351 A | 5/1994 | Gerrone |
| 5,312,363 A | 5/1994 | Ryan et al. |
| 5,334,147 A | 8/1994 | Johnson |
| 5,336,192 A | 8/1994 | Palestrant |
| 5,346,498 A | 9/1994 | Greelis et al. |
| 5,370,655 A | 12/1994 | Burns |
| 5,380,283 A | 1/1995 | Johnson |
| 5,383,892 A | 1/1995 | Cardon et al. |
| 5,387,235 A | 2/1995 | Chuter |
| 5,391,172 A | 2/1995 | Williams et al. |
| 5,399,164 A | 3/1995 | Snoke et al. |
| 5,405,378 A | 4/1995 | Strecker et al. |
| 5,411,507 A | 5/1995 | Heckele |
| 5,415,664 A | 5/1995 | Pinchuk |
| 5,417,708 A | 5/1995 | Hall et al. |
| 5,421,955 A | 6/1995 | Lau et al. |
| 5,433,723 A | 7/1995 | Lindenberg et al. |
| 5,443,477 A | 8/1995 | Marin et al. |
| 5,445,646 A | 8/1995 | Euteneuer et al. |
| 5,449,366 A | 9/1995 | Li |
| 5,449,373 A | 9/1995 | Pinchasik et al. |
| 5,456,694 A | 10/1995 | Marin et al. |
| 5,456,713 A | 10/1995 | Chuter |
| 5,458,615 A | 10/1995 | Klemm et al. |
| 5,466,221 A | 11/1995 | Zadini et al. |
| 5,470,315 A | 11/1995 | Adams |
| 5,477,856 A | 12/1995 | Lundquist |
| 5,480,423 A | 1/1996 | Ravenscroft et al. |
| 5,484,444 A | 1/1996 | Braunschweiler et al. |
| 5,507,751 A | 4/1996 | Goode et al. |
| 5,507,768 A | 4/1996 | Lau et al. |
| 5,507,769 A | 4/1996 | Marin et al. |
| 5,509,900 A | 4/1996 | Kirkman |
| 5,514,154 A | 5/1996 | Lau et al. |
| 5,531,690 A | 7/1996 | Solar |
| 5,534,007 A | 7/1996 | St. Germain et al. |
| 5,536,248 A | 7/1996 | Weaver et al. |
| 5,538,510 A | 7/1996 | Fontirroche et al. |
| 5,542,924 A | 8/1996 | Snoke et al. |
| 5,556,389 A | 9/1996 | Liprie |
| 5,562,726 A | 10/1996 | Chuter |
| 5,562,728 A | 10/1996 | Lazarus et al. |
| 5,569,296 A | 10/1996 | Marin et al. |
| 5,571,086 A | 11/1996 | Kaplan et al. |
| 5,571,172 A | 11/1996 | Chin |
| 5,573,530 A | 11/1996 | Fleury et al. |
| 5,578,074 A | 11/1996 | Mirigian |
| 5,591,172 A | 1/1997 | Bachmann et al. |
| 5,591,196 A | 1/1997 | Marin et al. |
| 5,601,568 A | 2/1997 | Chevillon et al. |
| 5,603,721 A | 2/1997 | Lau et al. |
| 5,603,801 A | 2/1997 | Defriese et al. |
| 5,605,530 A | 2/1997 | Fischell et al. |
| 5,609,627 A | 3/1997 | Goicoechea et al. |
| 5,618,300 A | 4/1997 | Marin et al. |
| 5,628,755 A | 5/1997 | Heller et al. |
| 5,630,801 A | 5/1997 | Roussigne et al. |
| 5,645,076 A | 7/1997 | Yoon |
| 5,649,906 A | 7/1997 | Gory et al. |
| 5,666,970 A | 9/1997 | Smith |
| 5,669,936 A | 9/1997 | Lazarus |
| 5,672,179 A | 9/1997 | Garth et al. |
| 5,674,208 A | 10/1997 | Berg et al. |
| 5,674,278 A | 10/1997 | Boneau |
| 5,681,322 A | 10/1997 | Hartigan, Jr. |
| 5,683,345 A | 11/1997 | Waksman et al. |
| 5,683,451 A | 11/1997 | Lenker et al. |
| 5,690,644 A | 11/1997 | Yurek et al. |
| 5,693,084 A | 12/1997 | Chuter |
| 5,695,498 A | 12/1997 | Tower |
| 5,695,499 A | 12/1997 | Helgerson et al. |
| 5,695,517 A | 12/1997 | Marin et al. |
| 5,697,936 A | 12/1997 | Shipko et al. |
| 5,697,949 A | 12/1997 | Giurtino et al. |
| 5,704,914 A | 1/1998 | Stocking et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,713,948 A | 2/1998 | Uflacker |
| 5,716,365 A | 2/1998 | Goicoechea et al. |
| 5,716,393 A | 2/1998 | Lindenberg et al. |
| 5,720,776 A | 2/1998 | Chuter et al. |
| 5,725,534 A | 3/1998 | Rasmussen |
| 5,728,158 A | 3/1998 | Lau et al. |
| 5,733,267 A | 3/1998 | Del Toro |
| 5,733,303 A | 3/1998 | Israel et al. |
| 5,735,893 A | 4/1998 | Lau et al. |
| 5,738,667 A | 4/1998 | Solar |
| 5,741,298 A | 4/1998 | MacLeod |
| 5,743,876 A | 4/1998 | Swanson |
| 5,749,921 A | 5/1998 | Lenker et al. |
| 5,755,777 A | 5/1998 | Chuter |
| 5,759,186 A | 6/1998 | Bachmann et al. |
| 5,766,184 A | 6/1998 | Matsuno et al. |
| 5,769,871 A | 6/1998 | Mers Kelly et al. |
| 5,776,141 A | 7/1998 | Klein et al. |
| 5,776,142 A | 7/1998 | Gunderson |
| 5,776,161 A | 7/1998 | Globerman |
| 5,776,186 A | 7/1998 | Uflacker |

(56) References Cited

U.S. PATENT DOCUMENTS

| | | |
|---|---|---|
| 5,780,807 A | 7/1998 | Saunders |
| 5,782,855 A | 7/1998 | Lau et al. |
| 5,788,707 A | 8/1998 | Del Toro et al. |
| 5,795,325 A | 8/1998 | Valley et al. |
| 5,800,456 A | 9/1998 | Maeda et al. |
| 5,800,520 A | 9/1998 | Fogarty et al. |
| 5,807,241 A | 9/1998 | Heimberger et al. |
| 5,807,327 A | 9/1998 | Green et al. |
| 5,810,768 A | 9/1998 | Lopez |
| 5,810,837 A | 9/1998 | Hofmann et al. |
| 5,810,869 A | 9/1998 | Kaplan et al. |
| 5,810,872 A | 9/1998 | Kanesaka et al. |
| 5,814,062 A | 9/1998 | Sepetka et al. |
| 5,824,058 A | 10/1998 | Ravenscroft et al. |
| 5,833,694 A | 11/1998 | Poncet |
| 5,840,064 A | 11/1998 | Liprie |
| 5,843,088 A | 12/1998 | Barra et al. |
| 5,843,092 A | 12/1998 | Heller et al. |
| 5,843,120 A | 12/1998 | Israel et al. |
| 5,843,244 A | 12/1998 | Pelton et al. |
| 5,851,210 A | 12/1998 | Torossian |
| 5,860,998 A | 1/1999 | Robinson et al. |
| RE36,104 E | 2/1999 | Solar |
| 5,868,755 A | 2/1999 | Kanner et al. |
| 5,873,906 A | 2/1999 | Lau et al. |
| 5,879,382 A | 3/1999 | Boneau |
| 5,891,154 A | 4/1999 | Loeffler |
| 5,904,648 A | 5/1999 | Arndt et al. |
| 5,906,579 A | 5/1999 | Vander Salm et al. |
| 5,906,619 A | 5/1999 | Olson et al. |
| 5,910,145 A | 6/1999 | Fischell et al. |
| 5,913,897 A | 6/1999 | Corso, Jr. et al. |
| 5,919,225 A | 7/1999 | Lau et al. |
| 5,925,061 A | 7/1999 | Ogi et al. |
| 5,928,246 A | 7/1999 | Gordon et al. |
| 5,931,842 A | 8/1999 | Goldsteen et al. |
| 5,944,727 A | 8/1999 | Ahari et al. |
| 5,951,585 A | 9/1999 | Cathcart et al. |
| 5,954,729 A | 9/1999 | Bachmann et al. |
| 5,961,536 A | 10/1999 | Mickley et al. |
| 5,968,052 A | 10/1999 | Sullivan, III et al. |
| 5,968,053 A | 10/1999 | Revelas |
| 5,968,061 A | 10/1999 | Mirza |
| 5,968,068 A | 10/1999 | Dehdashtian et al. |
| 5,968,069 A | 10/1999 | Dusbabek et al. |
| 5,972,018 A | 10/1999 | Israel et al. |
| 5,980,515 A | 11/1999 | Tu |
| 5,984,225 A | 11/1999 | Enzinna |
| 5,992,000 A | 11/1999 | Humphrey et al. |
| 5,997,562 A | 12/1999 | Zadno-azizi et al. |
| 6,004,328 A | 12/1999 | Solar |
| 6,015,429 A | 1/2000 | Lau et al. |
| 6,019,778 A | 2/2000 | Wilson et al. |
| 6,027,509 A | 2/2000 | Schatz et al. |
| 6,039,744 A | 3/2000 | Forber |
| 6,039,749 A | 3/2000 | Marin et al. |
| 6,042,597 A | 3/2000 | Kveen et al. |
| 6,045,536 A | 4/2000 | Meier et al. |
| 6,056,063 A | 5/2000 | Hung |
| 6,071,263 A | 6/2000 | Kirkman |
| 6,071,286 A | 6/2000 | Mawad |
| 6,077,295 A | 6/2000 | Limon et al. |
| 6,080,140 A | 6/2000 | Swaminathan et al. |
| 6,083,194 A | 7/2000 | Lopez |
| 6,090,035 A | 7/2000 | Campbell et al. |
| 6,090,063 A | 7/2000 | Makower et al. |
| 6,090,128 A | 7/2000 | Douglas |
| 6,096,009 A | 8/2000 | Windheuser et al. |
| 6,096,045 A | 8/2000 | Del Toro et al. |
| 6,096,056 A | 8/2000 | Brown |
| 6,102,890 A | 8/2000 | Stivland et al. |
| 6,102,942 A | 8/2000 | Ahari |
| 6,110,191 A | 8/2000 | Dehdashtian et al. |
| 6,113,607 A | 9/2000 | Lau et al. |
| 6,117,140 A | 9/2000 | Munsinger |
| 6,117,165 A | 9/2000 | Becker |
| 6,117,167 A | 9/2000 | Goicoechea et al. |
| 6,123,723 A | 9/2000 | Konya et al. |
| 6,129,755 A | 10/2000 | Mathis et al. |
| 6,136,007 A | 10/2000 | Goldsteen et al. |
| 6,136,572 A | 10/2000 | Benatti et al. |
| 6,143,014 A | 11/2000 | Dehdashtian et al. |
| 6,143,021 A | 11/2000 | Staehle |
| 6,146,415 A | 11/2000 | Fitz |
| 6,149,680 A | 11/2000 | Shelso et al. |
| 6,156,053 A | 12/2000 | Gandhi et al. |
| 6,156,054 A | 12/2000 | Zadno-azizi et al. |
| 6,156,063 A | 12/2000 | Douglas |
| 6,159,228 A | 12/2000 | Frid et al. |
| 6,159,239 A | 12/2000 | Greenhalgh |
| 6,167,315 A | 12/2000 | Coe et al. |
| 6,168,610 B1 | 1/2001 | Marin et al. |
| 6,168,617 B1 | 1/2001 | Blaeser et al. |
| 6,174,327 B1 | 1/2001 | Mertens et al. |
| 6,183,509 B1 | 2/2001 | Dibie |
| 6,190,360 B1 | 2/2001 | Iancea et al. |
| 6,190,393 B1 | 2/2001 | Bevier et al. |
| 6,190,406 B1 | 2/2001 | Duerig et al. |
| 6,203,550 B1 | 3/2001 | Olson |
| 6,203,558 B1 | 3/2001 | Dusbabek et al. |
| 6,210,422 B1 | 4/2001 | Douglas |
| 6,214,026 B1 | 4/2001 | Lepak et al. |
| 6,217,585 B1 | 4/2001 | Houser et al. |
| 6,224,608 B1 | 5/2001 | Ciccolella et al. |
| 6,238,402 B1 | 5/2001 | Sullivan, III et al. |
| 6,238,415 B1 | 5/2001 | Sepetka et al. |
| 6,238,837 B1 | 5/2001 | Fan |
| 6,241,692 B1 | 6/2001 | Tu et al. |
| 6,245,100 B1 | 6/2001 | Davila et al. |
| 6,248,122 B1 | 6/2001 | Klumb et al. |
| 6,251,132 B1 | 6/2001 | Ravenscroft et al. |
| 6,254,608 B1 | 7/2001 | Solar |
| 6,264,689 B1 | 7/2001 | Colgan et al. |
| 6,270,521 B1 | 8/2001 | Fischell et al. |
| 6,273,879 B1 | 8/2001 | Keith et al. |
| 6,273,895 B1 | 8/2001 | Pinchuk et al. |
| 6,287,322 B1 | 9/2001 | Zhu et al. |
| 6,312,407 B1 | 11/2001 | Zadno-azizi et al. |
| 6,315,794 B1 | 11/2001 | Richter |
| 6,319,262 B1 | 11/2001 | Bates et al. |
| 6,332,403 B1 | 12/2001 | Weise et al. |
| 6,342,067 B1 | 1/2002 | Mathis et al. |
| 6,344,053 B1 | 2/2002 | Boneau |
| 6,346,118 B1 | 2/2002 | Baker et al. |
| 6,348,065 B1 | 2/2002 | Brown et al. |
| 6,358,274 B1 | 3/2002 | Thompson |
| 6,368,344 B1 | 4/2002 | Fitz |
| 6,375,676 B1 | 4/2002 | Cox |
| 6,383,211 B1 | 5/2002 | Staehle |
| 6,391,050 B1 | 5/2002 | Broome |
| 6,391,051 B2 | 5/2002 | Sullivan, III et al. |
| 6,395,020 B1 | 5/2002 | Ley et al. |
| 6,402,760 B1 | 6/2002 | Fedida |
| 6,413,269 B1 | 7/2002 | Bui et al. |
| 6,425,898 B1 | 7/2002 | Wilson et al. |
| 6,443,979 B1 | 9/2002 | Stalker et al. |
| 6,443,982 B1 | 9/2002 | Israel et al. |
| 6,461,381 B2 | 10/2002 | Israel et al. |
| 6,471,673 B1 | 10/2002 | Kastenhofer |
| 6,488,703 B1 | 12/2002 | Kveen et al. |
| 6,500,248 B1 | 12/2002 | Hayashi |
| 6,514,261 B1 | 2/2003 | Randall et al. |
| 6,517,569 B2 | 2/2003 | Mikus et al. |
| 6,520,938 B1 | 2/2003 | Funderburk et al. |
| 6,520,983 B1 | 2/2003 | Colgan et al. |
| 6,527,779 B1 | 3/2003 | Rourke |
| 6,527,789 B1 | 3/2003 | Lau et al. |
| 6,544,278 B1 | 4/2003 | Vrba et al. |
| 6,569,181 B1 | 5/2003 | Burns |
| 6,572,643 B1 | 6/2003 | Gharibadeh |
| 6,575,993 B1 | 6/2003 | Yock |
| 6,582,459 B1 | 6/2003 | Lau et al. |
| 6,582,460 B1 | 6/2003 | Cryer |
| 6,599,296 B1 | 7/2003 | Gillick et al. |

(56) References Cited

U.S. PATENT DOCUMENTS

| | | |
|---|---|---|
| 6,613,014 B1 | 9/2003 | Chi |
| 6,613,075 B1 | 9/2003 | Healy et al. |
| 6,629,981 B2 | 10/2003 | Bui et al. |
| 6,645,237 B2 | 11/2003 | Klumb et al. |
| 6,645,238 B2 | 11/2003 | Smith |
| 6,652,506 B2 | 11/2003 | Bowe et al. |
| 6,659,977 B2 | 12/2003 | Kastenhofer |
| 6,660,031 B2 | 12/2003 | Tran et al. |
| 6,660,827 B2 | 12/2003 | Loomis et al. |
| 6,663,660 B2 | 12/2003 | Dusbabek et al. |
| 6,663,666 B1 | 12/2003 | Quiachon et al. |
| 6,695,862 B2 | 2/2004 | Cox et al. |
| 6,716,190 B1 | 4/2004 | Glines et al. |
| 6,716,238 B2 | 4/2004 | Elliott |
| 6,749,627 B2 | 6/2004 | Thompson et al. |
| 6,755,854 B2 | 6/2004 | Gillick et al. |
| 6,755,856 B2 | 6/2004 | Fierens et al. |
| 6,773,446 B1 | 8/2004 | Dwyer et al. |
| 6,786,918 B1 | 9/2004 | Krivoruchko et al. |
| 6,821,292 B2 | 11/2004 | Pazienza et al. |
| 6,860,898 B2 | 3/2005 | Stack et al. |
| 6,866,669 B2 | 3/2005 | Buzzard et al. |
| 6,884,259 B2 | 4/2005 | Tran et al. |
| 6,911,039 B2 | 6/2005 | Shiu et al. |
| 6,913,613 B2 | 7/2005 | Schwarz et al. |
| 6,926,732 B2 | 8/2005 | Derus et al. |
| 6,929,663 B2 | 8/2005 | Rioux et al. |
| 6,939,352 B2 | 9/2005 | Buzzard et al. |
| 6,939,370 B2 | 9/2005 | Hartley et al. |
| 6,997,870 B2 | 2/2006 | Couvillon, Jr. |
| 7,025,773 B2 | 4/2006 | Gittings et al. |
| 7,033,368 B2 | 4/2006 | Rourke |
| 7,052,511 B2 | 5/2006 | Weldon et al. |
| 7,122,050 B2 | 10/2006 | Randall et al. |
| 7,169,170 B2 | 1/2007 | Widenhouse |
| 7,169,175 B2 | 1/2007 | Cottone, Jr. et al. |
| 7,172,617 B2 | 2/2007 | Colgan et al. |
| 7,278,998 B2 | 10/2007 | Gaschino et al. |
| 7,285,130 B2 | 10/2007 | Austin |
| 7,294,135 B2 | 11/2007 | Stephens et al. |
| 7,323,006 B2 | 1/2008 | Andreas et al. |
| 7,326,236 B2 | 2/2008 | Andreas et al. |
| 7,356,903 B2 | 4/2008 | Krivoruchko et al. |
| 7,381,216 B2 | 6/2008 | Buzzard et al. |
| D576,725 S | 9/2008 | Shumer |
| D578,216 S | 10/2008 | Dorn et al. |
| D578,643 S | 10/2008 | Shumer et al. |
| D578,644 S | 10/2008 | Shumer et al. |
| D578,645 S | 10/2008 | Shumer et al. |
| 7,465,288 B2 | 12/2008 | Dudney et al. |
| 7,476,244 B2 | 1/2009 | Buzzard et al. |
| 7,506,650 B2 | 3/2009 | Lowe et al. |
| 7,540,880 B2 | 6/2009 | Nolting |
| 7,550,001 B2 | 6/2009 | Dorn et al. |
| 7,553,322 B2 | 6/2009 | Dorn et al. |
| 7,556,641 B2 | 7/2009 | Cully et al. |
| D598,543 S | 8/2009 | Vogel et al. |
| 7,582,054 B2 | 9/2009 | Okada |
| 7,637,932 B2 | 12/2009 | Bolduc et al. |
| 7,674,282 B2 | 3/2010 | Wu et al. |
| 7,758,625 B2 | 7/2010 | Wu et al. |
| 7,780,716 B2 | 8/2010 | Pappas et al. |
| 7,780,717 B2 | 8/2010 | Ducke et al. |
| 7,794,489 B2 | 9/2010 | Shumer et al. |
| 7,799,065 B2 | 9/2010 | Pappas |
| 7,815,669 B2 | 10/2010 | Matsuoka et al. |
| 7,819,882 B2 | 10/2010 | Rourke |
| 7,879,080 B2 | 2/2011 | Sato |
| 7,931,670 B2 | 4/2011 | Fiehler et al. |
| 7,935,141 B2 | 5/2011 | Randall et al. |
| 7,967,829 B2 | 6/2011 | Gunderson et al. |
| 7,976,574 B2 | 7/2011 | Papp |
| 7,993,384 B2 | 8/2011 | Wu et al. |
| 8,062,344 B2 | 11/2011 | Dorn et al. |
| 8,075,606 B2 | 12/2011 | Dorn |
| 8,075,823 B2 | 12/2011 | Guggenbichler et al. |
| 8,197,528 B2 | 6/2012 | Colgan et al. |
| 8,216,296 B2 | 7/2012 | Wu et al. |
| 8,382,813 B2 | 2/2013 | Shumer |
| 8,419,784 B2 | 4/2013 | Matsuoka et al. |
| 8,486,128 B2 | 7/2013 | Jen et al. |
| 8,500,789 B2 | 8/2013 | Wuebbeling et al. |
| 8,518,098 B2 | 8/2013 | Roeder et al. |
| 8,702,778 B2 | 4/2014 | Loewen |
| 8,808,346 B2 | 8/2014 | Jimenez, Jr. et al. |
| 8,888,834 B2 | 11/2014 | Hansen et al. |
| 9,078,799 B2 | 7/2015 | Shohat et al. |
| 9,149,379 B2 | 10/2015 | Keady et al. |
| 9,211,206 B2 | 12/2015 | Pryor |
| 9,421,115 B2 | 8/2016 | Wubbeling et al. |
| 9,801,745 B2 | 10/2017 | Wubbeling et al. |
| 9,901,469 B2 | 2/2018 | Dorn et al. |
| 10,206,800 B2 | 2/2019 | Wubbeling et al. |
| 2001/0007082 A1 | 7/2001 | Dusbabek et al. |
| 2001/0044621 A1 | 11/2001 | Klumb et al. |
| 2001/0049549 A1 | 12/2001 | Boylan et al. |
| 2001/0051822 A1 | 12/2001 | Stack et al. |
| 2002/0004663 A1 | 1/2002 | Gittings et al. |
| 2002/0035394 A1 | 3/2002 | Fierens et al. |
| 2002/0045929 A1 | 4/2002 | Diaz |
| 2002/0052642 A1 | 5/2002 | Cox et al. |
| 2002/0095203 A1 | 7/2002 | Thompson et al. |
| 2002/0116044 A1 | 8/2002 | Cottone et al. |
| 2002/0128678 A1 | 9/2002 | Petersen |
| 2002/0151955 A1* | 10/2002 | Tran .................. A61F 2/95 623/1.12 |
| 2002/0183827 A1 | 12/2002 | Derus et al. |
| 2002/0188341 A1 | 12/2002 | Elliott |
| 2003/0028236 A1 | 2/2003 | Gillick et al. |
| 2003/0049295 A1 | 3/2003 | Guggenbichler et al. |
| 2003/0050686 A1 | 3/2003 | Raeder-Devens et al. |
| 2003/0074043 A1 | 4/2003 | Thompson |
| 2003/0074045 A1 | 4/2003 | Buzzard et al. |
| 2003/0105451 A1 | 6/2003 | Westlund et al. |
| 2003/0135162 A1 | 7/2003 | Deyette et al. |
| 2003/0163085 A1 | 8/2003 | Tanner et al. |
| 2003/0163193 A1 | 8/2003 | Widenhouse |
| 2003/0167060 A1 | 9/2003 | Buzzard et al. |
| 2003/0191516 A1 | 10/2003 | Weldon et al. |
| 2003/0208262 A1 | 11/2003 | Gaber |
| 2004/0006380 A1 | 1/2004 | Buck et al. |
| 2004/0098079 A1 | 5/2004 | Hartley et al. |
| 2004/0098083 A1 | 5/2004 | Tran et al. |
| 2004/0143160 A1 | 7/2004 | Couvillon |
| 2004/0148009 A1 | 7/2004 | Buzzard et al. |
| 2004/0153137 A1 | 8/2004 | Gaschino et al. |
| 2004/0163650 A1 | 8/2004 | Lowe et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0193283 A1 | 9/2004 | Rioux et al. |
| 2004/0199240 A1 | 10/2004 | Dorn |
| 2005/0004515 A1 | 1/2005 | Hart et al. |
| 2005/0021123 A1* | 1/2005 | Dorn .................. A61F 2/95 623/1.11 |
| 2005/0027306 A1 | 2/2005 | Krivoruchko et al. |
| 2005/0027345 A1 | 2/2005 | Horan et al. |
| 2005/0033402 A1 | 2/2005 | Cully et al. |
| 2005/0043618 A1 | 2/2005 | Mansouri-Ruiz |
| 2005/0043713 A1 | 2/2005 | Zhou |
| 2005/0060016 A1 | 3/2005 | Wu et al. |
| 2005/0080476 A1 | 4/2005 | Gunderson et al. |
| 2005/0085851 A1 | 4/2005 | Fiehler et al. |
| 2005/0090887 A1 | 4/2005 | Pryor |
| 2005/0090890 A1 | 4/2005 | Wu et al. |
| 2005/0149159 A1* | 7/2005 | Andreas .............. A61F 2/95 623/1.11 |
| 2005/0159725 A1 | 7/2005 | Tockman et al. |
| 2005/0182475 A1 | 8/2005 | Jen et al. |
| 2005/0209670 A1 | 9/2005 | George et al. |
| 2005/0209672 A1 | 9/2005 | George et al. |
| 2005/0209674 A1 | 9/2005 | Kutscher et al. |
| 2005/0240254 A1 | 10/2005 | Austin |
| 2005/0256562 A1 | 11/2005 | Clerc et al. |

(56) References Cited

U.S. PATENT DOCUMENTS

| | | |
|---|---|---|
| 2005/0273151 A1 | 12/2005 | Fulkerson et al. |
| 2005/0288764 A1 | 12/2005 | Snow et al. |
| 2005/0288766 A1 | 12/2005 | Plain et al. |
| 2006/0058866 A1 | 3/2006 | Cully et al. |
| 2006/0074477 A1 | 4/2006 | Berthiaume et al. |
| 2006/0085057 A1 | 4/2006 | George et al. |
| 2006/0093643 A1 | 5/2006 | Stenzel |
| 2006/0095050 A1 | 5/2006 | Hartley et al. |
| 2006/0095116 A1 | 5/2006 | Bolduc et al. |
| 2006/0100686 A1 | 5/2006 | Bolduc et al. |
| 2006/0100687 A1 | 5/2006 | Fahey et al. |
| 2006/0167467 A1 | 7/2006 | Rourke |
| 2006/0173525 A1 | 8/2006 | Behl et al. |
| 2006/0241737 A1 | 10/2006 | Tockman et al. |
| 2006/0259124 A1 | 11/2006 | Matsuoka et al. |
| 2006/0276873 A1 | 12/2006 | Sato |
| 2007/0016164 A1 | 1/2007 | Dudney et al. |
| 2007/0050006 A1 | 3/2007 | Lavelle |
| 2007/0055339 A1 | 3/2007 | George et al. |
| 2007/0055342 A1 | 3/2007 | Wu et al. |
| 2007/0060999 A1 | 3/2007 | Randall et al. |
| 2007/0061007 A1 | 3/2007 | Nolting |
| 2007/0073379 A1 | 3/2007 | Chang |
| 2007/0073389 A1 | 3/2007 | Bolduc et al. |
| 2007/0088421 A1 | 4/2007 | Loewen |
| 2007/0100420 A1 | 5/2007 | Kavanagh et al. |
| 2007/0100422 A1 | 5/2007 | Shumer et al. |
| 2007/0100429 A1 | 5/2007 | Wu et al. |
| 2007/0112409 A1 | 5/2007 | Wu et al. |
| 2007/0118201 A1 | 5/2007 | Pappas et al. |
| 2007/0118206 A1 | 5/2007 | Colgan et al. |
| 2007/0156222 A1 | 7/2007 | Feller et al. |
| 2007/0156224 A1 | 7/2007 | Cioanta et al. |
| 2007/0168014 A1* | 7/2007 | Jimenez ............... A61F 2/95 623/1.12 |
| 2007/0191864 A1 | 8/2007 | Shumer |
| 2007/0191865 A1 | 8/2007 | Pappas |
| 2007/0191925 A1 | 8/2007 | Dorn |
| 2007/0194483 A1 | 8/2007 | Guggenbichler et al. |
| 2007/0233222 A1 | 10/2007 | Roeder et al. |
| 2007/0244540 A1 | 10/2007 | Pryor |
| 2007/0255390 A1 | 11/2007 | Ducke et al. |
| 2008/0140175 A1* | 6/2008 | Boucher ............... A61F 2/95 623/1.11 |
| 2008/0188920 A1 | 8/2008 | Moberg et al. |
| 2009/0024133 A1 | 1/2009 | Keady et al. |
| 2009/0024137 A1 | 1/2009 | Chuter et al. |
| 2009/0099638 A1 | 4/2009 | Grewe |
| 2010/0004606 A1 | 1/2010 | Hansen et al. |
| 2010/0036472 A1 | 2/2010 | Papp |
| 2010/0094399 A1 | 4/2010 | Dorn et al. |
| 2010/0145429 A1 | 6/2010 | Dhoke et al. |
| 2010/0161024 A1 | 6/2010 | Kennedy, II et al. |
| 2010/0168756 A1 | 7/2010 | Dorn et al. |
| 2010/0174290 A1 | 7/2010 | Wuebbeling et al. |
| 2011/0213410 A1 | 9/2011 | Ginn et al. |
| 2013/0211493 A1 | 8/2013 | Wubbeling et al. |
| 2013/0317592 A1 | 11/2013 | Wubbeling et al. |
| 2014/0330362 A1 | 11/2014 | Jimenez, Jr. et al. |
| 2015/0320579 A1 | 11/2015 | Wubbeling et al. |
| 2018/0049899 A1 | 2/2018 | Wubbeling et al. |
| 2019/0159917 A1 | 5/2019 | Wubbeling et al. |

FOREIGN PATENT DOCUMENTS

| | | |
|---|---|---|
| DE | 3132323 A1 | 4/1983 |
| DE | 3219629 A1 | 12/1983 |
| DE | 2544371 C2 | 7/1985 |
| DE | 4133696 A1 | 4/1993 |
| DE | 4420142 A1 | 12/1995 |
| DE | 29516712 U1 | 12/1995 |
| DE | 19539449 A1 | 4/1997 |
| DE | 29717110 U1 | 11/1997 |
| DE | 29816878 U1 | 12/1998 |
| DE | 29522101 U1 | 12/1999 |
| DE | 19921530 | 6/2000 |
| DE | 19901530 A1 | 7/2000 |
| DE | 19936059 A1 | 2/2001 |
| DE | 20000659 U1 | 5/2001 |
| DE | 69521346 T2 | 4/2002 |
| EP | 0436303 A1 | 7/1991 |
| EP | 0505686 A1 | 9/1992 |
| EP | 0518838 A1 | 12/1992 |
| EP | 0564894 A1 | 10/1993 |
| EP | 0611556 A1 | 8/1994 |
| EP | 0630657 A1 | 12/1994 |
| EP | 0633756 A1 | 1/1995 |
| EP | 0752896 A1 | 3/1995 |
| EP | 0792627 B2 | 6/1995 |
| EP | 1290989 A3 | 9/1995 |
| EP | 0688545 A1 | 12/1995 |
| EP | 0699451 A2 | 3/1996 |
| EP | 0712614 A1 | 5/1996 |
| EP | 0790041 B1 | 7/1996 |
| EP | 0744930 A1 | 12/1996 |
| EP | 0747021 A2 | 12/1996 |
| EP | 0752896 B1 | 1/1997 |
| EP | 0790041 A2 | 8/1997 |
| EP | 0792627 A2 | 9/1997 |
| EP | 0873733 A1 | 4/1998 |
| EP | 0876804 A1 | 5/1998 |
| EP | 0947212 A2 | 3/1999 |
| EP | 1117341 A1 | 9/1999 |
| EP | 1447057 A1 | 9/1999 |
| EP | 1447058 A1 | 9/1999 |
| EP | 1025813 A3 | 2/2000 |
| EP | 1078611 A1 | 3/2000 |
| EP | 1132058 A1 | 3/2000 |
| EP | 1095634 A3 | 10/2000 |
| EP | 1078611 A1 | 2/2001 |
| EP | 1155664 B1 | 5/2001 |
| EP | 1299050 A2 | 6/2001 |
| EP | 1181906 A3 | 8/2001 |
| EP | 1199051 A3 | 10/2001 |
| EP | 1383446 B1 | 4/2002 |
| EP | 1637092 A3 | 4/2002 |
| EP | 1302178 B1 | 10/2002 |
| EP | 1440671 A3 | 12/2003 |
| EP | 2179709 B1 | 8/2006 |
| FR | 2760351 B1 | 3/1997 |
| FR | 2797781 B1 | 8/1999 |
| FR | 2797761 A1 | 3/2001 |
| JP | 2003518406 A1 | 12/2000 |
| JP | 2005530558 A | 6/2003 |
| JP | 2004147812 A | 5/2004 |
| JP | 2005532100 A | 10/2005 |
| JP | 2007-097620 A | 4/2007 |
| JP | 2007-508045 A | 4/2007 |
| MX | 303207 | 12/2012 |
| WO | 1995012593 A1 | 11/1994 |
| WO | 1995026775 A1 | 3/1995 |
| WO | 1996018359 A1 | 11/1995 |
| WO | 1996018361 A1 | 6/1996 |
| WO | 1998020811 A1 | 11/1997 |
| WO | 1998023241 A3 | 11/1997 |
| WO | 1998030173 A1 | 1/1998 |
| WO | 1998009584 A1 | 3/1998 |
| WO | 1999051167 A3 | 4/1998 |
| WO | 1998052496 A1 | 5/1998 |
| WO | 1999004728 A1 | 7/1998 |
| WO | 1999025280 A8 | 11/1998 |
| WO | 1999044541 A1 | 2/1999 |
| WO | 1999047075 A1 | 3/1999 |
| WO | 2000000104 A1 | 6/1999 |
| WO | 2000002503 A1 | 7/1999 |
| WO | 2000016718 A1 | 9/1999 |
| WO | 2000018330 A1 | 9/1999 |
| WO | 2001032102 A1 | 4/2000 |
| WO | 2000071059 A1 | 5/2000 |
| WO | 2000078246 A2 | 6/2000 |
| WO | 2000078248 A1 | 6/2000 |
| WO | 2000067675 A1 | 11/2000 |
| WO | 2000069368 A2 | 11/2000 |

(56) References Cited

FOREIGN PATENT DOCUMENTS

| | | | |
|---|---|---|---|
| WO | 2001034061 A1 | 11/2000 |
| WO | 2000078248 A1 | 12/2000 |
| WO | 2001047436 A2 | 12/2000 |
| WO | 2001058387 A1 | 2/2001 |
| WO | 2001089421 A2 | 5/2001 |
| WO | 2002003888 A3 | 6/2001 |
| WO | 2002003889 A3 | 7/2001 |
| WO | 2002066094 A2 | 12/2001 |
| WO | 2002083036 A2 | 12/2001 |
| WO | 2002087470 A1 | 4/2002 |
| WO | 2002102279 A2 | 6/2002 |
| WO | 2003002020 A2 | 6/2002 |
| WO | 2003003926 A1 | 1/2003 |
| WO | 2003061724 A2 | 1/2003 |
| WO | 2005004515 A8 | 6/2003 |
| WO | 2004004597 A2 | 1/2004 |
| WO | 2005039448 A1 | 6/2004 |
| WO | 2004066809 A2 | 8/2004 |
| WO | 2005053574 A3 | 11/2004 |
| WO | 2005062980 A2 | 12/2004 |
| WO | 2005065200 A2 | 12/2004 |
| WO | 2005117759 A3 | 6/2005 |
| WO | 2006104143 A1 | 3/2006 |
| WO | 2007002713 A2 | 6/2006 |
| WO | 2007005799 A1 | 6/2006 |
| WO | 2006071915 A2 | 7/2006 |
| WO | 2007022395 A1 | 8/2006 |
| WO | 2007029242 A1 | 9/2006 |
| WO | 2007044929 A1 | 10/2006 |
| WO | 2007083470 A1 | 12/2006 |
| WO | 2008034793 A1 | 9/2007 |
| WO | 2010027998 A1 | 3/2010 |

OTHER PUBLICATIONS

Jan. 19, 2007 International Search Report in international application No. PCT/US2006/032228 filed on Aug. 16, 2006.
Jan. 19, 2007 Written Opinion of the ISA in international application No. PCT/US2006/032228 filed on Aug. 16, 2006.
Feb. 20, 2008 International Preliminary Report on Patentability in international application No. PCT/US2006/032228 filed on Aug. 16, 2006.
Jul. 10, 2002 International Search Report in international application No. PCT/EP2002/04727 filed on Apr. 29, 2002.
Jan. 7, 2003 International Preliminary Examination Report in international application No. PCT/EP2002/04727 filed on Apr. 29, 2002.
Jan. 21, 2004 International Search Report in international application No. PCT/EP2002/06784 filed on Jun. 19, 2002.
Apr. 14, 2004 International Preliminary Examination Report in international application No. PCT/EP2002/06784 filed on Jun. 19, 2002.
"Medtronic Announces FDA Clearance of Bridge SE Biliary Stent." Business Wire, Oct 15, 2001. www.medtronic.com/newsroom/news20011015a.html.
Dec. 15, 2005 International Search Report in international application No. PCT/US2005/019860 filed on Jun. 6, 2005.
Dec. 15, 2005 Written Opinion of the international searching authority in international application No. PCT/US2005/019860 filed on Jun. 6, 2005.
Dec. 4, 2006 International Preliminary Report on Patentability in international application No. PCT/US2005/019860 filed on Jun. 6, 2005.
Apr. 27, 2007 International Search Report in international application No. PCT/US2007/000834 filed on Jan. 12, 2007.
Apr. 27, 2007 Written Opinion of the ISA in international application No. PCTUS2007000834 filed on Jan. 12, 2007.
Jul. 15, 2008 International Preliminary Report on Patentability in international application No. PCTUS2007000834 filed on Jan. 12, 2007.
Bridge SE Binary System, Oct. 2002, 3 pages, http:/www.medtronicave/com/includes/content/phsycians/bridges/htm.

Nov. 30, 2007 International Search Report in international application No. PCT/EP2007/058205 filed on Aug. 7, 2007.
Nov. 30, 2007 Written Opinion of the International Searching Authority in international application No. PCT/EP2007/058205 filed on Aug. 7, 2007.
Aug. 4, 2008 International Preliminary Report on Patentability in international application No. PCT/EP2007/058205 filed on Aug. 7, 2007.
Nov. 4, 2008 International Search Report in international application No. PCT/EP2008/059040 filed on Jul. 10, 2008.
Nov. 4, 2008 Written Opinion of the ISA in international application No. PCT/EP2008/059040 filed on Jul. 10, 2008.
Sep. 29, 2009 International Preliminary Report on Patentability in international application No. PCT/EP2008/059040 filed on Jul. 10, 2008.
EP 10001359.8 filed Aug. 16, 2006 European Search Report dated May 28, 2010.
EP 13170019.7 extended European Search Report dated Aug. 5, 2013.
EP 14151266.5 Extended European Search Report dated Apr. 9, 2014.
EP 14151266.5 filed Jan. 14, 2014, Examination Report dated Oct. 2, 2018.
JP 2008-550429 filed Jun. 27, 2008 Final Notice of Reason for Rejection dated Oct. 25, 2012.
JP 2008-550429 filed Jun. 27, 2008 Office Action dated Jan. 4, 2012.
JP 2010-515514 Notice of Reason for Rejection dated Dec. 20, 2012.
JP 2013-011060 first Official Action dated Feb. 21, 2014.
JP 2013-089100 Official Action dated Apr. 8, 2014.
PCT/EP2011/068238 filed Oct. 19, 2011 International Preliminary Report on Patentability dated Apr. 23, 2013.
U.S. Appl. No. 10/476,351, filed May 7, 2004 Final Office Action dated Feb. 4, 2009.
U.S. Appl. No. 10/476,351, filed May 7, 2004 Final Office Action dated Oct. 21, 2008.
U.S. Appl. No. 10/476,351, filed May 7, 2004 Notice of Allowance dated Mar. 12, 2009.
U.S. Appl. No. 10/476,351, filed May 7. 2004 Non-Final Office Action dated Apr. 4, 2008.
U.S. Appl. No. 10/824,033, filed Apr. 14, 2004 Non-Final Office Action dated Jul. 17, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26. 2009.
U.S. Appl. No. 11/505,185, filed Aug. 16, 2006 Non-Final Office Action dated Mar. 31, 2010.
U.S. Appl. No. 11/505,185, filed Aug. 16, 2006 Non-Final Office Action dated Aug. 31, 2009.
U.S. Appl. No. 11/505,185, filed Aug. 16, 2006 Non-Final Office Action dated Oct. 7, 2010.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated May 27, 2009.
U.S. Appl. No. 11/652,737, filed Jan. 12, 2007 Final Office Action dated Jun. 10, 2010.
U.S. Appl. No. 11/652,737, filed Jan. 12, 2007 Non-Final Office Action dated Oct. 27, 2009.
U.S. Appl. No. 11/652,737, filed Jan. 12, 2007 Non-Final Office Action dated Nov. 12, 2008.

(56) References Cited

OTHER PUBLICATIONS

U.S. Appl. No. 11/652,737, filed Jan. 12, 2007 Non-Final Office Action dated Apr. 12, 2013.
U.S. Appl. No. 11/652,737, filed Jan. 12, 2007 Non-Final Office Action dated Feb. 12, 2014.
U.S. Appl. No. 11/652,737, filed Jan. 12, 2007 Advisory Action dated Dec. 30, 2011.
U.S. Appl. No. 11/652,737, filed Jan. 12, 2007 Final Office Action dated Oct. 22, 2013.
U.S. Appl. No. 11/652,737, filed Jan. 12, 2007 Notice of Allowance dated Apr. 25, 2014.
U.S. Appl. No. 12/376,670, filed Feb. 6, 2009 Final Office Action dated Dec. 17, 2013.
U.S. Appl. No. 12/376,670, filed Feb. 6, 2009 Non-Final Office Action dated Aug. 5, 2014.
U.S. Appl. No. 12/376,670, filed Feb. 6, 2009 Non-Final Office Action dated Jun. 21, 2012.
U.S. Appl. No. 12/376,670, filed Feb. 6, 2009 Notice of Allowance dated Mar. 23, 2015.
U.S. Appl. No. 12/640,956, filed Dec. 17, 2009 Non-Final Office Action dated Jan. 24, 2011.
U.S. Appl. No. 12/640,956, filed Dec. 17, 2009 Notice of Allowancwe dated Jul. 13, 2011.
U.S. Appl. No. 12/668,613, filed Feb. 19, 2010 Non-Final Office Action dated Nov. 26, 2012.
U.S. Appl. No. 13/878,187, filed Apr. 5, 2013 Advisory Action dated May 11, 2016.
U.S. Appl. No. 13/878,187, filed Apr. 5, 2013 Final Office dated Dec. 30, 2015.
U.S. Appl. No. 13/878,187, filed Apr. 5, 2013 Non-Final Office Action dated Jan. 13, 2017.
U.S. Appl. No. 13/878,187, filed Apr. 5, 2013 Non-Final Office dated Apr. 24, 2015.
U.S. Appl. No. 13/878,187, filed Apr. 5, 2013 Notice of Allowance dated Jun. 28, 2017.
U.S. Appl. No. 13/958,460, filed Aug. 2, 2013 Non-Final Office Action dated Dec. 4, 2015.
U.S. Appl. No. 13/958,460, filed Aug. 2, 2013 Notice of Allowance dated Apr. 22, 2016.
U.S. Appl. No. 14/793,669, filed Jul. 7, 2015 Non-Final Office Action dated Jun. 21, 2017.
U.S. Appl. No. 14/793,669, filed Jul. 7, 2015 Notice of Allowance dated Oct. 23, 2017.
U.S. Appl. No. 14/793,659, filed Jul. 7, 2015 Non-Final Office Action dated Jan. 10, 2018.
U.S. Appl. No. 14/793,659, filed Jul. 7, 2015 Non-Final Office Action dated Jun. 30, 2017.
U.S. Appl. No. 14/793,659, filed Jul. 7, 2015 Notice of Allowance dated Oct. 5, 2018.
U.S. Appl. No. 15/473,420, filed Mar. 29, 2017 Final Office Action dated Sep. 9, 2019.
U.S. Appl. No. 15/473,420, filed Mar. 29, 2017 Non-Final Office Action dated Feb. 6, 2019.
U.S. Appl. No. 15/473,420, filed Mar. 29, 2017 Non-Final Office Action dated Jun. 25, 2020.
U.S. Appl. No. 15/473,420, filed Mar. 29, 2017 Non-Final Office Action dated Sep. 26, 2018.
U.S. Appl. No. 15/798,315, filed Oct. 30, 2017 Non-Final Office Action dated Aug. 7, 2019.
U.S. Appl. No. 15/798,315, filed Oct. 30, 2017 Final Office Action dated Mar. 3, 2020.

* cited by examiner

Fig. 1

HAND-HELD ACTUATOR DEVICE

This application is a continuation of U.S. application Ser. No. 14/793,669, filed Jul. 7, 2015, now U.S. Pat. No. 9,901,469, which is a divisional of U.S. application Ser. No. 12/376,670, filed Feb. 6, 2009, now U.S. Pat. No. 9,078,779, which is a U.S. national stage application under 35 U.S.C. § 371 of International Application No. PCT/EP2007/058205, filed Aug. 7, 2007, claiming priority to Great Britain Patent Application No. 0615658.2, filed Aug. 7, 2006, each of which is incorporated by reference in its entirety into this application.

FIELD OF THE INVENTION

The present invention relates generally to a catheter based system for treating a remote location within a patient and more particularly to the hand-held actuator devices of stent delivery systems.

BACKGROUND

A delivery system for a self-expanding stent usually has the stent distally adjacent to a tube, both within a sleeve at the distal end of a catheter. To deliver the stent, the sleeve has to be pulled back while the tube holds the stent from moving back with the sleeve. Therefore, the tube is placed adjacent to the stent and acts as a barrier and restrains the stent from moving while the sleeve is pulled back.

WO 02/087470 discloses a hand device for a catheter stent delivering system. The hand device can be operated one-handed to ease the operation with such a device. The main function such devices have to include are:
1) to pull back the sleeve, for example by pulling a wire which is connected to the proximal end of the outer sleeve;
2) to restrain simultaneously the inner tube from being pulled back together with the sleeve; and
3) to provide a visual signal of how much length of the sleeve has already been pulled back The restraint function can be performed by a hub that is mounted within the hand-held actuator and itself receives the proximal end of the tube. To pull the wire, in WO 02/087470 is provided an index-finger-triggering-system, which causes a mechanical apparatus within the device to pull in the wire and draw the proximal end of the sleeve into the housing of the hand unit. A disadvantage of the index-finger-triggering-system is that it is a pistol-like device and the impression it gives to the operator, of direct tactile feedback about the progress of stent release, some operators might find unconvincing. Furthermore, the maximum length of wire, which can be reeled in by successive squeezes of the trigger, is defined by the length of the. track in the hand unit along which the proximal end of the sleeve advances proximally, rendering it incapable of releasing a self-expanding stent which is longer than the track.

EP 1 299 050 discloses a thumb-actuating-screwing-system, but this has all disadvantages of the index-finger-triggering-system. In addition the thumb has to be lifted between every turn of the screw, which makes the control of the pull-mechanism less comfortable.

Both of the above identified systems have a component protruding from the housing of the hand unit, which moves proximally through the device with the catheter being withdrawn, and so acts as a distance indicator. When the operator starts coiling-up the wire, the indicator moves and the operator and his or her assistants can judge the extent of the progressive stent release from the distance the indicator has travelled proximally along the length of the housing of the hand unit.

Stents are getting longer (e.g. in a leg the stent can be about 30 cm). It is one object of the present invention to provide a hand-held actuator for release of a self-expanding stent with a length longer than can be handled by the known hand-held actuators.

Generally, the present invention aims to improve on the performance of the devices of WO 02/087470 and EP 1 299 056, in the respects mentioned above.

SUMMARY OF THE INVENTION

According to the present invention there is provided a device for releasing into the body from a delivery system a medical prosthesis, like a stent, of the form discussed herein. Optional or preferred features of the invention are mentioned in the claims.

In a first preferred embodiment, the device comprises a frame, which can be moulded of plastic and acts as housing. At its distal end a hub is provided, which acts as an abutment system for the tube. A slider is connected in a one-way connection to a reel, which is caused to rotate by a pull stroke of the slider. The reel winds a portion of a length of the wire by every pull stroke and holds the position by every return stroke. A detent restrains the reel from moving during a return stroke, so the reel is urged to move in only one direction.

In a second embodiment the slider is formed as a thumb pad and has a carriage portion on his flanks. It slides on a track, which is defined by the frame. In a rest position, the slider is restrained from sliding by a slider release element, which is located within the thumb pad and which prevents the wire inadvertently being pulled proximally. In the restraining initial position the slider release element protrudes from the carriage portion of the slider. The slider release element can be urged in a second release position, which allows the slider to move free on the track.

Particularly when the slider slides on a track in a direction parallel to the axis of the catheter, the operator has the sensation that the thumb pad delivers useful tactile feedback about what happening at the distal end of the catheter, where the stent is being released.

In a third embodiment, the one-way connection comprises teeth on a elongation of the slider element and co-operating teeth on a rotatory element which is operatively connected to the reel. The one-way connection could be located between the teeth of the slider and the rotatory element. In this case the teeth are formed such that they engage in one way and slip over in the reverse direction. Such embodiment can enhance the sensation of tactile feedback to the operator, through the wire and reel to the slider.

In another embodiment the detent is formed as a pawl to engage with the reel or, more specifically, with the teeth of the rotatory element, to restrain it from moving in the reverse direction. This finger preferably points in the rotatory direction of the wheel. In another construction of the detent a finger engages with the wire such that the finger pushes the wire onto the reel. In this case the restraining force comes from the resilience of the wire in addition to the friction between the wire and the finger. In a further embodiment, the detent comprises both the pawl and the finger. Embodiments that include such a pawl can provide audible feedback to the operator (and others working with the operator}, in the form of clicking sounds, about the rate of progress of the stent release operation.

These embodiments can be used with stent delivery catheters, both 'over the wire' and 'rapid exchange'. They can be used regardless whether it is the inner or the outer element of the co-axial shaft of the catheter which is proximally withdrawn relative to the other to release the stent. A catheter system which employs the inner of two co-axial shaft elements to pull proximally back a sheath that surrounds a self-expanding stent at the distal end of the catheter is called a 'pull-wire' stent delivery catheter. Such a pull wire system is useful for delivering ultra-long stents, because the reel can accommodate a length of the pull wire longer than the stent, however long the stent is.

The described embodiments need very few mechanical elements. This avoids unnecessary waste and minimizes assembly time and weight of the device. Furthermore, with the pull wire of the catheter system connected directly to the reel there is no limit to the length of wire that can be withdrawn proximally. With relatively short stents, when placement in the body is delicate, the slider can still act as an indicator of stent release progress, and how much of the stent length is still to be released.

The design of the device can be formed ergonomically such it is comfortable for every hand size of any operator. In addition, the thumb of the gripping hand falls naturally on the thumb pad of the slider.

Recapitulating some advantages of the present invention over the above mentioned prior art systems are:
better tactile feedback about the stent delivery progress
no limitation of the stent length, with simultaneous visual information about the stent delivery progress stepless wire-pulling and audible feedback of the operation progress
improved handling through ergonomic design reduced number of mechanical components

DETAILED DESCRIPTION

The invention can be embodied in a device for pulling a wire 8 out of a tube 14 and which can be activated, preferably with only one hand.

Figure 1:
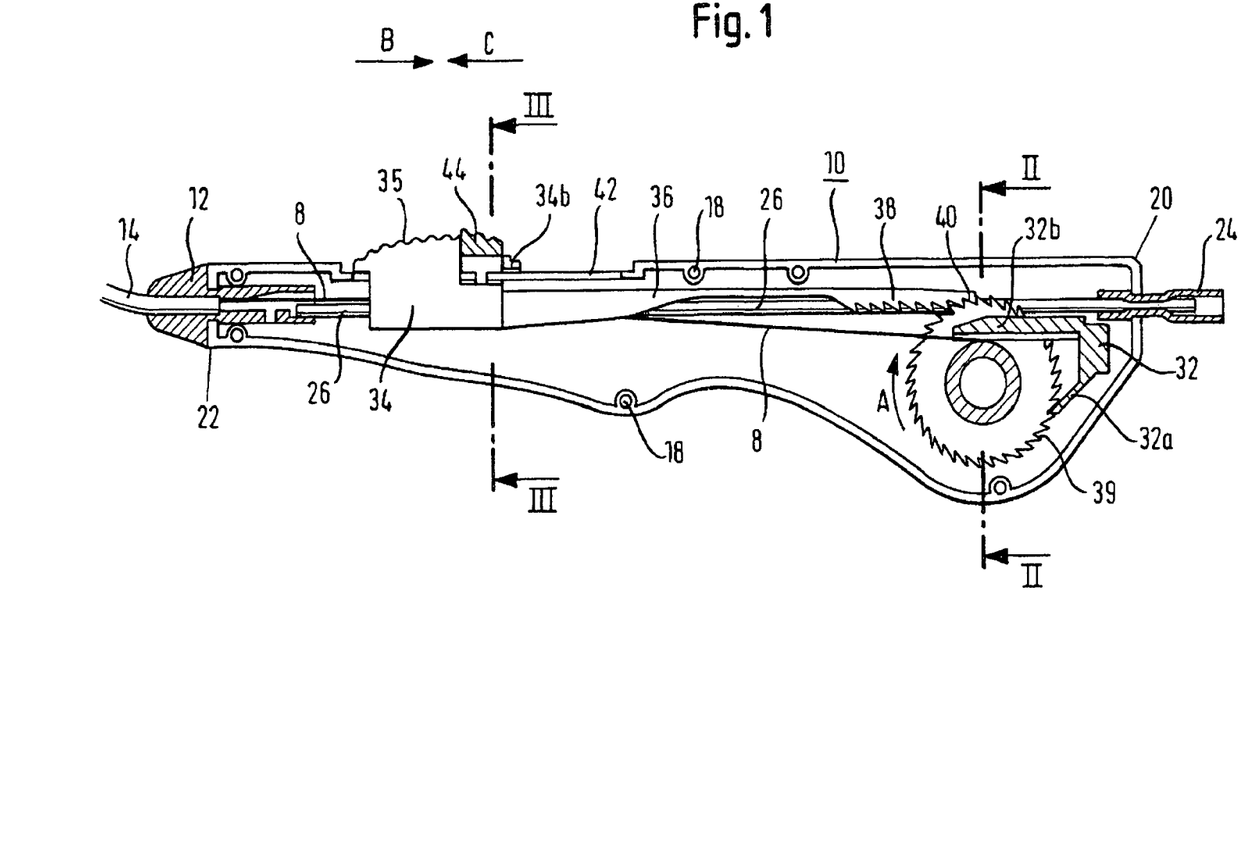
FIG. 1 shows a longitudinal section of a preferred embodiment.

The drawings show a preferred embodiment of the invention. FIG. 1 shows one half of a molded housing 10 which serves as a frame for mounting the various components of the device, and has a proximal end 20 and a distal end 22. The housing is almost symmetric and the two half housing parts are fixed together with screws 18 (or something similar like rivets or plugs) at defined places. A portion of each half of the housing is covered with a rubber material (not shown). This increases the grip and eases the handling of the device.

A first hub 12 is fixed at the distal end 22 of the housing, acting as an abutment and bearing element for guiding the tube 14 to the housing 10. The tube 14 terminates in the hub 12, so that a wire 8 can be pulled out of the tube. The hub 12 acts as an abutment element and stops the tube 14 from being pulled into the housing 10. Through this abutment element extends an inner tube 26 to a second hub 24 at the proximal end 20 of the housing 10. The second hub 24 provides a female luer connector to engage a corresponding male luer, for flushing liquid for the lumen of the tube 14.

Figure 3:
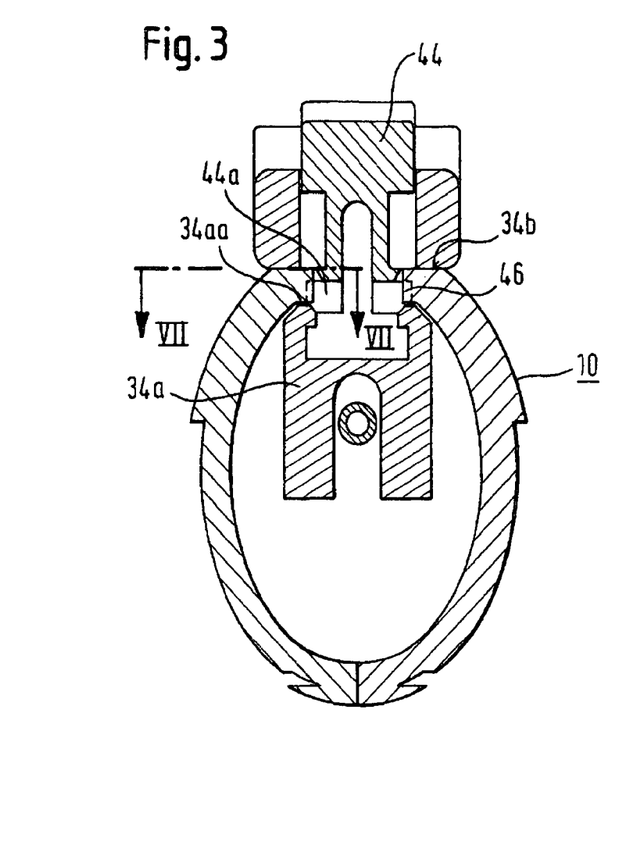
FIG. 3 shows a transverse section along the line III-III in FIG. 1.

A reel 30 is provided to take up the wire 8 and is preferably near the proximal end 20 of the housing 10 rotatably mounted in the housing. The reel is flanked by two large discs 30a, 30b, spaced apart by a cylindrical drum surface 30c of the reel for the wire. Both of the discs have a toothed circumferential surface to provide a ratchet element (see FIG. 3). In other embodiments there could be only one smooth wheel and one ratchet wheel instead of both wheels being ratchet wheels.

The reel coils up the wire when it rotates in the direction of arrow A and would release the wire if it were able to rotate in the opposite direction.

Figure 4:
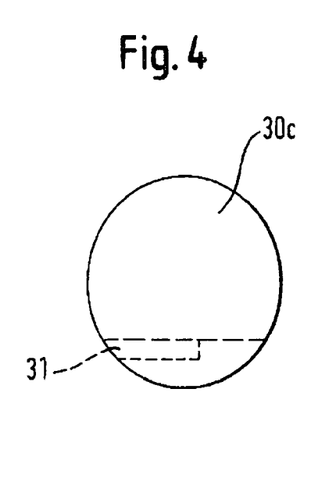
FIG. 4 is a side view to show a borehole and a groove in the cylindrical drum of the reel.
Figure 5:
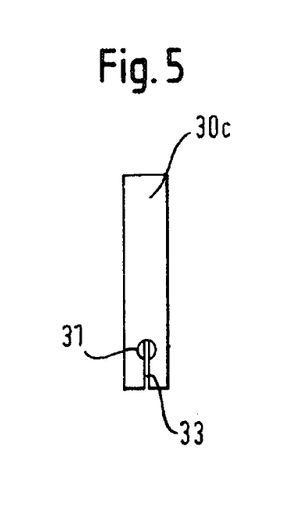
FIG. 5 is a front view of the drum of FIG. 4.
Figure 6:
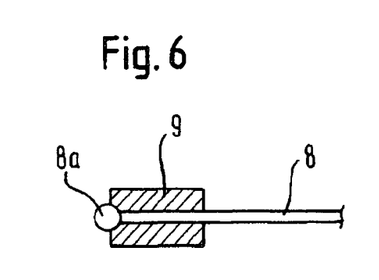
FIG. 6 is a side view of an end of the wire.

To attach the wire 8 to the reel 30 there is provided a special ball-end on the wire and 8 a borehole in the drum With reference to FIGS. 4, 5 and 6 a borehole 31 is provided in the cylindrical drum 30c. The borehole 31 leads from the surface of the cylindrical drum 30c, in a direction transverse to the rotatory axis into the drum 30c, to an abutment surface 31c. A groove 33 co-axial with the borehole 31 links the borehole with the surface of the drum.

The end of the wire 8 carries a sleeve 9 and a ball Ba, welded to the end of the wire 8. The wire B is put with the free end into the sleeve 9 and the ball Sa stops the wire 8 from sliding through the sleeve 9. Another way fixing the 8 sleeve 9 to the wire 8 could be to weld the ball Sa on the wire 8 after putting it through the sleeve 9.

In another embodiment the wire and the sleeve are pressed together such the sleeve 9 is fixed on the wire.

The wire 8 is threaded into the groove 33 and the sleeve 9 is advanced into the borehole 31. Pulling the wire urges the sleeve to slide into the first borehole 31a, which has a diameter slightly bigger than the sleeve 9, and blocks the wire from being pulled further.

To avoid releasing a coiled up wire, a backstroke-stopper 32 (otherwise called 'detent') is provided near the reel 30. In the preferred embodiment the stopper has two fingers. The first is a detent 32a which functions as a pawl by engaging the teeth of the ratchets 30a and/or 30b. The teeth of the ratchets are so shaped that the finger 32a does not prevent the ratchet from rotating in direction A, but stops the reel rotating in the other direction by engaging into a gap between adjacent teeth.

Figure 2:
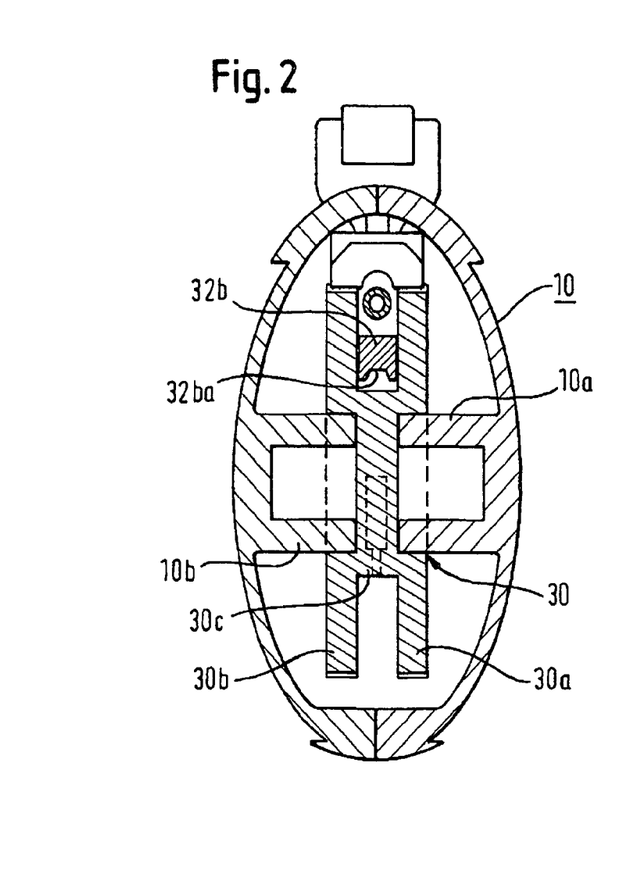
FIG. 2 shows a transverse section along the line II-II in FIG. 1.

The second finger 32b serves to press the already coiled wire towards the rotational axis of the reel. The wire is springy so it tends to straighten when it can and so will tend to unroll from the reel. The second finger prevents this happening. Preferably the second finger 32b has a recess 32ba (as shown in FIG. 2) facing the wire to receive the wire 8. When the second finger 32b presses down the wire 8, there is friction between the wire and the finger. This friction, together with the resilience of the wire, can act as a brake in the rotation of the reel. Indeed, such a brake can render any ratchet and pawl superfluous. One advantage of a brake over a ratchet in that one can achieve a stepless pulling of the wire 8.

To urge the reel to rotate to wind in the wire 8, in direction A, a slider 34 is provided. This slider has a thumb pad 35 and is operably connected to the reel by its elongate extension 36 that has a toothed straight ratchet profile 38 at its end remote from the thumb pad. The toothed straight profile 38 and the toothed ratchet on the periphery of each of the reel discs 30a, 30b provide a one-way-connection 40 in which the reel rotates when the slider is moved in the direction of arrow B. When the discs are so urged to rotate, the drum 30c between the two discs is also rotating and the wire is coiled up. When the slider is urged in the reverse direction, arrow C, the teeth of the straight ratchet slide over the teeth of the discs (see 40). In another embodiment the straight ratchet and the discs may be fixedly connected such that both move together, in both directions. A one-way bearing in the hub of the reel allows the wire take-up reel to rotate in the direction of arrow A, but not in direction of arrow B. Of course the movement directions of the particular elements are changeable at will. For example, if the wire coils up anti-clockwise on the reel, rather than clockwise, each would be arranged the other way.

Figure 7:
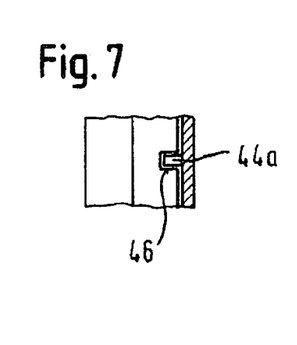
FIG. 7 is a section along the line IV-IV in FIG. 3 seen from above.

The slider slides on a track 42, defined by the housing 10. The slider includes a slider release element 44, that is moveable between a relaxed gripping disposition and a pushed down release disposition. The release element, when not pushed down, is formed such that a detent 44a of the slider release element is blocked by a recess 46 the housing (as shown in FIG. 7). This restrains inadvertent sliding of the slider. When the slider is to be moved, the slider release element is first pushed down until the detent engages the corresponding locker element 34aa on the inner part of the slider 34a and is being held down. As a result the slider 34 is released from the recess 46 in the housing and is free to move along the track 42.

In another embodiment there could be provided a distance scale (not shown) next to the sliding track advancing the distance indication by the slider.

In another embodiment, there is provided a spring (not shown) in the housing 10, which is connected to the slider and urges the slider to slide back into the first pull back position automatically.

As soon as the slider release element 44 is no longer pushed down, it moves up again as a result of its resilience and the ramps 44a and 34aa, once again to restrain slider movement.

In the present embodiment all device members (reel, housing, slider, head, hub and stopper) are molded from plastics. In other embodiments components can be provided as separate individual parts (e.g. the reel in one smooth, smaller wheel and two ratchets). These parts can be formed of various materials (e.g. metal, different kinds of plastics) and assembled (by screwing, plugging, welding, riveting) as desired.

What is claimed is:

1. A device for releasing into a body from a delivery system a medical prosthesis, comprising:
   a housing frame including a distal bearing hub;
   an inner housing tube communicating with the distal bearing hub, the inner housing tube extending through the housing frame to a proximal hub;
   a reel rotatably mounted to the housing frame adjacent the proximal hub, the reel designed to wind a wire extending into the housing frame through the distal bearing hub;
   a slider operably connected to the reel, the slider mounted to the housing frame;
   a connection comprising at least one reel disc that engages the slider and the reel during a backward stroke and that disengages the slider and the reel during a forward stroke; and
   a detent comprising a first end that engages the reel and a second end that engages the wire.

2. The device of claim 1, wherein the first end of the detent functions as a pawl by engaging the reel.

3. The device of claim 2, wherein the second end of the detent guides the wire toward the reel.

4. The device of claim 3, wherein the at least one reel disc includes a toothed circumferential surface.

5. The device of claim 1, further comprising a track mounted to the housing frame, wherein the slider is configured to slide along the track.

6. The device of claim 5, wherein the slider comprises a release element that is moveable between a relaxed gripping disposition and a pushed down release disposition.

7. The device of claim 1, wherein the at least one reel disc comprises a first reel disc and a second reel disc, and wherein the reel is flanked by the first reel disc and the second reel disc.

8. The device of claim 1, further comprising:
   a catheter having a proximal end extending through the distal bearing hub;
   a sheath disposed coaxially inside a distal end of the catheter and attached to the wire; and
   a self-expanding stent mounted in the sheath.

\* \* \* \* \*